United States Patent
Boehmer-Lasthaus et al.

(10) Patent No.: US 8,321,238 B2
(45) Date of Patent: Nov. 27, 2012

(54) METHOD AND SYSTEM FOR AUTOMATICALLY ASSOCIATING AN ASSESSOR WITH A MEDICAL ASSESSMENT TASK

(75) Inventors: Sonja Boehmer-Lasthaus, Nuremberg (DE); Rainer Kuth, Hoechstadt (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 509 days.

(21) Appl. No.: 12/480,817

(22) Filed: Jun. 9, 2009

(65) Prior Publication Data

US 2009/0307010 A1    Dec. 10, 2009

(30) Foreign Application Priority Data

Jun. 9, 2008    (DE) .......................... 10 2008 027 479

(51) Int. Cl.
  *G06Q 50/00* (2006.01)
(52) U.S. Cl. .................... 705/2; 705/3; 705/4; 705/7.21

(58) Field of Classification Search .................. 705/2–4, 705/7.21
See application file for complete search history.

(56) References Cited

U.S. PATENT DOCUMENTS

| | | | |
|---|---|---|---|
| 7,729,928 B2 * | 6/2010 | Backhaus et al. ................ 705/2 |
| 7,995,815 B2 * | 8/2011 | Nekrich ........................ 382/128 |
| 2002/0087382 A1 * | 7/2002 | Tiburcio .......................... 705/9 |
| 2003/0120544 A1 | 6/2003 | Gritzbach et al. |
| 2004/0153340 A1 * | 8/2004 | Christ et al. ..................... 705/2 |
| 2006/0159325 A1 * | 7/2006 | Zeineh et al. ................. 382/128 |
| 2007/0136095 A1 * | 6/2007 | Weinstein ........................ 705/2 |
| 2007/0162305 A1 * | 7/2007 | Miller ............................. 705/2 |
| 2007/0232885 A1 * | 10/2007 | Cook et al. .................... 600/407 |

* cited by examiner

*Primary Examiner* — Gerald J. O'Connor
*Assistant Examiner* — Mark Holcomb
(74) *Attorney, Agent, or Firm* — Schiff Hardin LLP

(57) ABSTRACT

In a method and system for automated association of an assessor with an assessment task (in particular an evaluation of an image data set) an assessor database is used that contains assessors as well as selection information associated with assessors and task information associated with assessment tasks. A medical assessment is automatically associated with an assessor using at least one decision rule, starting from the task information and with consideration of the relevant selection information.

29 Claims, 2 Drawing Sheets

METHOD AND SYSTEM FOR AUTOMATICALLY ASSOCIATING AN ASSESSOR WITH A MEDICAL ASSESSMENT TASK

BACKGROUND OF THE INVENTION

1. Field of the Invention

The present invention concerns a method to associate an assessor (or evaluator or diagnostician) with an assessment task, in particular an evaluation of an image data set.

2. Description of the Prior Art

In large hospitals (but also in large physicians' practices), a number of examinations (frequently even into the hundreds) are conducted daily. In order to be able to evaluate (i.e. to assess) data acquired in the examination (in particular with radiological modalities), specific qualifications of the assessor (typically a physician) are required, for example.

The greater the number of the assessment tasks, the more difficult it is to solve the organizational problem. A large number of assessors with varying qualifications and amounts of time available for assessments must be taken into account. It may occur that a physician with the necessary qualification is not present at all at the specific medical facility. An approximated equal allocation of the assessment tasks to the various assessors should also be achieved as much as possible.

In the conventional organization of a hospital, each physician has responsibility for one or more acquisition stations, for example a computed tomography apparatus or multiple acquisition raster tables. Depending on his or her level of training, the physician assesses the data alone or reviews it with a more qualified physician. A generalized quality assurance of the findings ensues by the director of the department cross-checking the findings now and again.

However, this procedure entails several disadvantages. The various assessors are frequently unevenly utilized since different modalities are visited by a different number of patients. The quality assurance additionally ensues subjectively as described, and there is no possibility at all to consult outside experts.

SUMMARY OF THE INVENTION

An object of the present invention is to provide a method that allows an improved, more cost-effective, and flexible and expandable but automated, an association of medical assessment with an assessor.

This object is achieved according to the invention by a method to associate an assessor with a medical assessment task (in particular an evaluation of an image data set) that uses an assessor database of assessors as well as selection information associated with the assessors, and a task database of medical assessment tasks as well as task information associated with the medical assessment tasks; and wherein a processor associates a medical assessment with an assessor starting from the task information and under consideration of the selection information using at least one decision rule.

A fully automatic method is accordingly achieved that no longer requires any user intervention at all to associate an assessment task with an assessor. The basis is two different databases, namely an assessor database of assessors with whom selection information is respectively associated and a task database of medical assessment tasks with which respective task information is associated. Using one or more decision rules, in particular linking rules, the information of both of these databases is now utilized in order to locate the most suitable assessor for an assessment task.

In addition to the examination data itself, the task database contains task information that essentially reflects the type of the finding to be conducted. Based on this task information it is possible to automatically select an assessor form the assessor database, with the selection information stored therein being taken into account. The selection information contains the qualifications of the assessor, his or her time constraints, or other data required for a proper and quality-assured association.

In particular a marked cost decrease is possible by the automated assignment of assessment tasks to assessors that is enabled in this way. A flexible system is additionally achieved in which various focal points can advantageously be emphasized through corresponding selection of the decision rules, for example an optimized utilization of the personnel, an excellent quality control and quality assurance, and a cost decrease in the task allocation.

In a further embodiment of the method the selection information is divided into one group of items of required selection information and one group of items of additional selection information. Within the scope of the association, assessors for whom at least one required item of task information exhibits a value that is incompatible with the task information and/or exhibits a value precluding an association, are initially excluded from the scope of the association, after which the association with a non-excluded assessor occurs using the additional selection information. Depending on the task information, specific required selection information must accordingly have a specific value in order to permit an assignment to this assessor to be considered at all. In an exclusion process, all users for whom the required values are not present, or for whom another exclusion reason is present (thus a required item of selection information exhibits a different value precluding an association), are accordingly initially precluded from the assessment. The most suitable assessor is then selected only from among the remaining assessors based on additional selection criteria, namely decision rules using the additional selection information. The additional selection information can accordingly also be viewed as "desirable" information.

For making such an initial exclusion, at least one qualification of the assessor and/or working hours of the assessor that remain for assessment tasks and/or at least one bar of the assessor from specific assessment tasks are used as required selection information. The qualification of the assessor is very significant for most assessment tasks and therefore can be directly applied as an exclusion criterion in the scope of the method according to the invention. An assessor can also be precluded when no more time for assessment tasks remains according to his or her schedule—for instance, because many assessment tasks have already been assigned to him or her. It can be additionally provided, however, that these decision rules are negated if an assessor with free assessment time is no longer found but an assessment must urgently be conducted. It is also possible that—for whatever reason—a physician is barred from specific assessment tasks although he or she possesses the necessary qualifications, for example.

Information about specific assessment tasks still to be conducted can be used as selection information in general (but in particular as additional selection information) to obtain a qualification and/or the necessary assignment of an additional assessor. In particular, physicians in training or new entrants into the workplace frequently require a specific number of completed assessments in order to obtain the qualification for a specific type of assessment tasks. In this type of training it is in most cases necessary for an additional assessor to be assigned who checks the finding produced by the assessor to be trained. or compares it with his or her own finding. Therefore, in an additional embodiment of the method when it is necessary to assign an additional assessor, this additional assessor is likewise assigned by the method, in particular using modified task information and/or modified decision rules. For example, the additional assessor should already possess the necessary qualification that is sought by the primary assessor, and/or be assigned to the primary assessor for supervision. An additional modified decision rule can cause a particularly experienced or particularly qualified additional assessor to be assigned. This can also be expressed by changing the task information, for example by, instead of a normal assessment task, requiring a control (supervised) assessment task. The primary assessor can additionally be informed of the finding of an additional assessor, and/or the quality of the finding of the primary assessor can be registered. In this way the method can additionally be used as a learning aid by the primary assessor can comparing the finding of the experienced additional assessor with his or her own assessment. Moreover, the performance of the primary assessor can be polled and monitored at any time, in particular also with regard to his or her attainment of the qualifications.

It is of particular advantage when the assessors of multiple medical facilities (in particular multiple hospitals and/or physicians' practices) are entered as assessors in the assessor database. Multiple significant advantages are achieved in this way. It is possible to utilize the expert potential of multiple medical facilities. Accordingly, if an expert for a specific assessment task is not present in a hospital or a physician's practice, such an expert can nevertheless be located outside of this medical facility. An outsourcing for medical assessment is additionally possible in a comfortable manner. It is thereby possible to reduce the workload of the assessors of a medical facility and cost savings maybe possible if outside assessors conduct the findings at a reduced price.

The method according to the invention can also embody an accounting component so that billing information that is used to charge for the assessment task is determined from the selection information and the task information. Such a functionality is particularly helpful when assessors of multiple medical facilities receive assignments to assessment tasks. In particular, an invoice that contains all necessary information can then be automatically included, generated and (automatically) mailed.

With the method according to the invention, findings can also be allocated according to economic criteria. Two advantageous alternatives of the method according to the invention are thereby to be cited for the design of the information, the decision rules or the final assignment.

The selection information includes at least one item of price information specifying the costs of the assessment task by the assessor. This affords the possibility of the price information being modified by the user, in particular during the assignment of an assessment task. The assessor accordingly has the possibility to adapt his or her price information to the respective market conditions at any time. The concept of a reverse auction can be advantageously applied. For this purpose, an assessor can be informed if a finding, for which he or she in particular possesses the necessary values for the required selection information is to be assigned to a different assessor. The informed assessor can react by correspondingly adapting his or her price information, whereupon the assignment is rechecked by the method. Using the decision rules, the selection information and the task information, a determination can be made as to how much the assessor must decrease his or her costs in order to receive the assigned assessment task, which amount is communicated to the user in the scope of the notification. In the method according to the invention, the price information at which the corresponding user would receive the assignment is thereby recalculated, and this value (or the equivalent difference) is communicated to the user. All embodiments known for an auction can be applied to this embodiment operating in the manner of a reverse auction; for example, a running time of the auction can be established, a live auction can occur, and the like. All types of interactivity are conceivable.

Furthermore, independent of the use of a reverse auction, a maximum price describing the maximum cost of the assessment task is used as the task information, and an assessor is precluded if his or her cost exceeds the maximum costs. Such a decision rule thus links the maximum price information and the price information of the assessor in order to define an additional exclusion criterion, so that an excessive price for a an assessment task is not thereby requested.

As an alternative to the embodiment with price information on the part of the assessor, the task information can include price information describing the remuneration to be paid to the assessor. In this way the remuneration for an assessment task can be established by the assigner directly. In a further embodiment, the price to be paid can be increased as time passes without finding an assessor. In this way it is ensured that even difficult, time-consuming findings ultimately find an assessor, even if the assessment task has previously been declined by the associated assessor.

In general, if information describing prices or costs is used, a virtual currency can be used in an embodiment of the invention for information describing the costs or prices. Such virtual currencies are frequently used in medical facilities since the actual monetary amounts are available only upon the allocation of a budget to the corresponding department responsible for the assessment task. An assessor thus initially receives accounting points, for example, that then can have different values depending on the budget assigned to the department.

The method according to the invention also offers excellent avenues for quality assurance. For example, a selectable portion (number) of the assessment tasks can be assigned to at least two assessors. For quality assurance, the findings of the at least two assessors can then be automatically inspected for agreement. Given a lack of agreement of the findings, the assessment task is assigned by the method to a third assessor (in particular using modified task information and/or modified decision rules), and the third assessor evaluates the findings for their correctness. The number or the proportion of wrong findings for specific finding types is stored in the database as selection information. Accordingly it is automatically, initially checked whether the findings (thus ultimately the diagnoses) agree. This can occur using the typical abbreviations for specific diagnoses, for example. The ICD code (International Statistical Classification of Diseases and Related Health Problems) is suitable for this purpose. If the comparison yields that the assessors came to different results, the assessment task is assigned by the method to a third assessor. The decision rules and/or the task information can then be modified, for example to cause an especially qualified person to receive the assignment of the assessment task. This third assessor then generates an additional finding (possibly even without knowledge of the results of the previous findings) that can be compared with the findings of the first two assessors, or the third assessor directly checks the findings of the first two assessors. If it results that a finding has been incorrect, this information is noted for the respective assessor. The assessment reliability of a given assessor thus can be checked at any time. This selection information may then possibly also be taken into account in the assignment of assessment tasks. An assessor may even become barred from an associated finding type, and/or measures can be recommended to the assessor to increase his or her qualifications if the assessor exceeds a limit value for incorrect findings and/or the proportion of incorrect findings. Such a bar can then be taken into account as required selection information through a corresponding decision rule. This simultaneously serves as a motivation tool for the assessor to take the recommended measures to improve his or her qualifications, for example to attend development curses or refresher courses. In this way the quality of the findings is sustainably ensured.

If selection information exists in specific areas, for example in price information, high assessment certainty, working toward a qualification, etc., it can be desirable to appropriately weight the selection information through the decision rules. The selection information thus can be provided with weighting factors. In this way the focal point of the selection can be shifted so that, for example, particularly favorably priced findings can be preferred over working toward a qualification, and the like.

Given the use of weighting factors, a numerical value is associated by the decision rules with every assessor (in particular every assessor who is not precluded), and the assessment task is assigned to the assessor with the lowest or the highest numerical value. In this method variant the evaluation of the assessor, which reflects his or her suitability for assignment of the assessment task) accordingly occurs using a numerical value. The weighting factors can advantageously enter into the calculation. Given a division into required and additional selection information, the assessors who are not precluded are accordingly determined first. These remaining assessors are thereupon evaluated according to the method according to the invention, to identify which assessor has achieved the lowest or the highest numerical value. The assessment task is then assigned to this assessor.

Several factors affecting the assignment can be taken into account in the decision rules, for example also via use of weighting factors. For example, the most recent obtainment of a qualification by an assessor, and/or the equal distribution of assessment tasks for all assessors, and/or the realization of an optimally inexpensive assessment task can be used as decision rules, configured by weighting factors.

Additional embodiments of the selection information are conceivable. Still-required assessments for the obtainment of a qualification and/or the time required for an assessment task thus can be used as selection information and be taken into account in the assignment.

To respect the private sphere of the patient and the confidentiality of data, personal data of a patient (in particular the name and/or the address and/or the birthday) are not communicated to the assessor given the presence of additional conditions. In particular if assessors who are normally unknown to the patient process an assessment task, it can be in the interest of the patient or data protection in general, when the assessor does not learn the identity of the patient. For example, this can be reasonable for quality assurance measures (if multiple assessors are selected) or testing measures. However, if assessors of multiple facilities are contained in the assessor database, the affiliation of the assessor with another facility can be used as an auxiliary condition. The patient data of a personal nature can thus not leave the corresponding medical facility.

In addition to the method, the invention also concerns a system for association of an assessor with an assessment task, in particular an evaluation of an image data set, comprising: an assessor database with assessors as well as selection information associated with assessors; a task database with assessment tasks as well as task information associated with assessment tasks; and a computer which is fashioned to assign an assessment task to an assessor via at least one decision rule, starting from the task information and under consideration of the selection information.

With such a system (wherein the computer can be fashioned as a central server that communicates with workstation computers over a network, in particular the Internet or an intranet) an assessment task is assigned to an assessor in a wholly automated manner. The computer can in principle be designed such that is fashioned to implement the method in all aforementioned embodiments.

Workstation computers of different medical facilities (in particular hospitals and/or medical practices) can be connected to the system. It is therefore possible to also incorporate assessors of outside medical facilities.

Furthermore, the task database can be part of a patient administration system. Such patient administration systems are known and can be typical hospital information systems. It is possible storage components for the task database to be distributed among multiple medical facilities. Systems are also suitable that centrally administer electronic patient records, for example. Such systems are known in the prior art.

DESCRIPTION OF THE PREFERRED EMBODIMENTS

Figure 1:
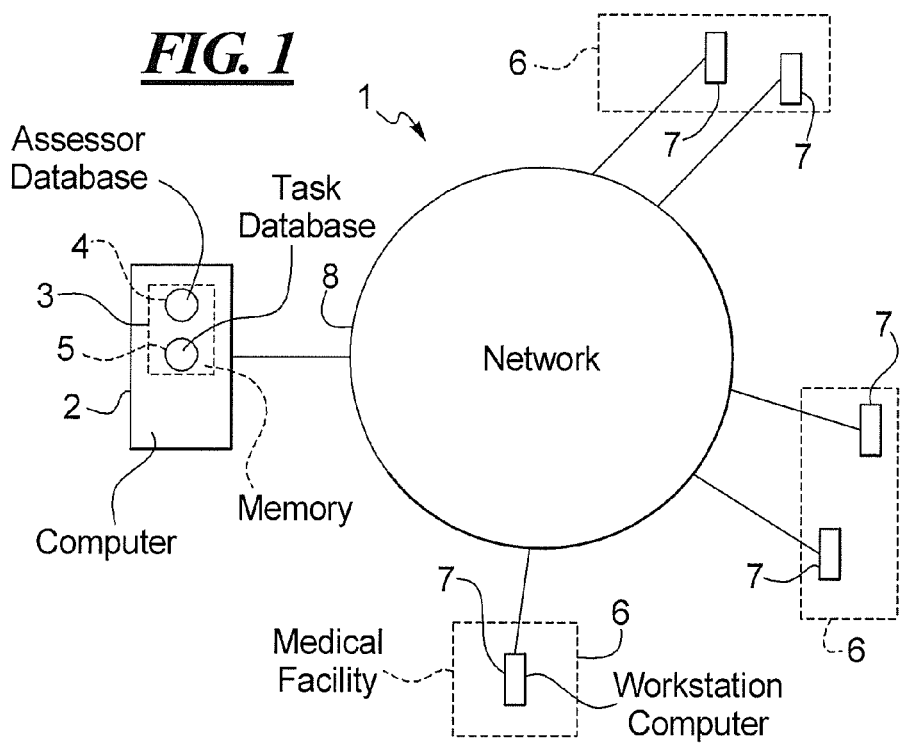
FIG. 1 schematically illustrates an embodiment of a system according to the invention.

FIG. 1 shows an embodiment of a system 1 according to the invention. The system includes a computer 2 (here a central server) in whose memory 3 an assessor database 4 and a task database 5 are stored. The task database 5 is thereby associated with a patient administration system.

Assessors as well as selection information associated with these are stored in the assessor database 4. Assessment tasks as well as task information associated with these are located in the task database 5. These assessment tasks and their associated task information originate from examinations in various medical facilities 6 that can comprise hospitals and medical practices, for example. The assessment tasks are in particular the evaluation of image data that, for example, were acquired with a computer tomography apparatus or a magnetic resonance device. The computer 2 communicates with the workstation computers 7 of the medical facilities 6 via a network 8, for example the Internet. In the scope of the method according to the invention the computer 2 is fashioned to associate an assessment task with an assessor via at least one decision rule and under consideration of the selection information, starting from the task information.

Figure 2:
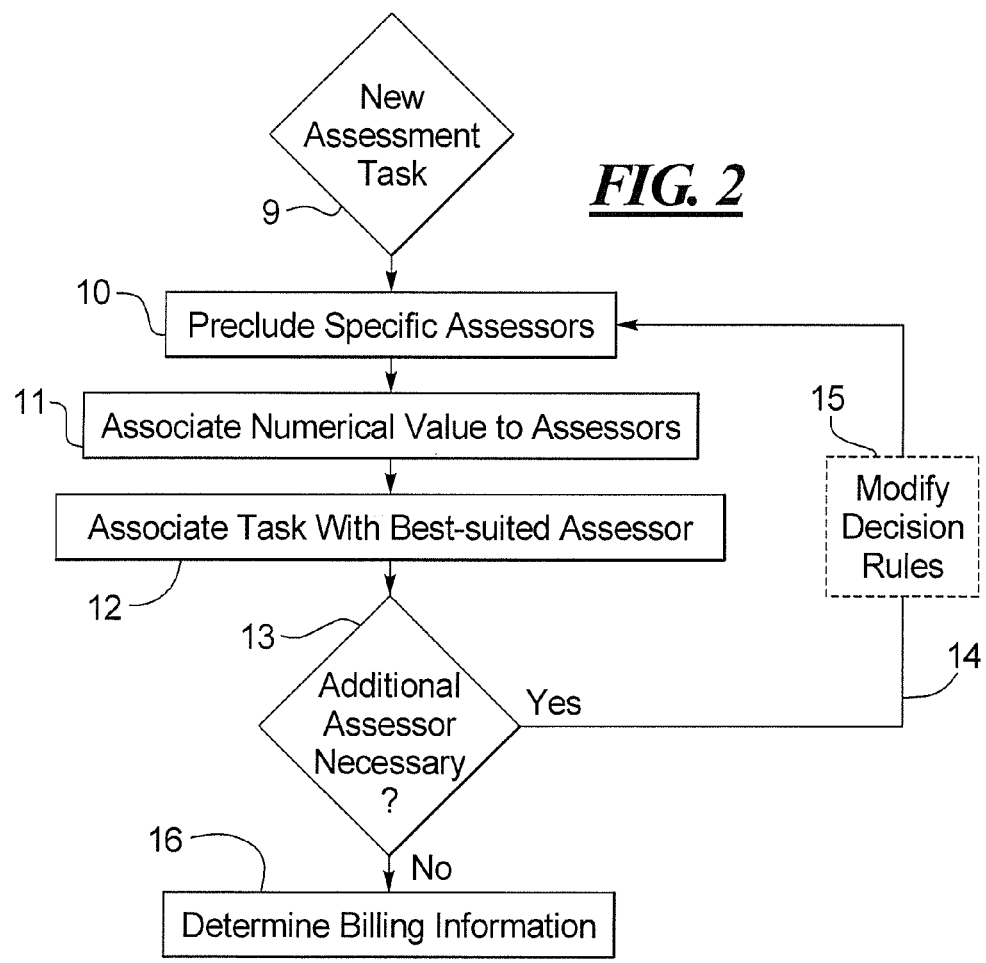
FIG. 2 is a flowchart of an embodiment of the method according to the invention.

FIG. 2 shows a flowchart of an embodiment of the method according to the invention. The method according to the invention is always implemented when a new assessment task is present in the task database 5 (Box 9).

The selection information in the assessor database 4 are divided into necessary selection information and additional selection information. In this example, various qualifications of the assessor that indicate for which type of assessment tasks the assessor is qualified, working hours of the assessor remaining for assessment tasks (the working hours are naturally adapted according to every assigned assessment task) and information that indicates whether the assessor is barred from specific assessment tasks are provided necessary selection information. Among other things, information about specific assessment tasks still to be conducted to obtain a qualification, the necessary assignment of an additional assessor, price information indicating the cost of the assessor for the assessment task, information about additional qualifications, information about the number or the proportion of correct findings, the necessary time for an assessment task and the affiliation of the assessor with a medical facility 6 are provided as additional selection information. An assessor is now associated with the assessment task using decision rules.

In Step 10 it is initially provided that specific assessors are precluded from the assessment task. The necessary selection information that was already mentioned serves for this. In Step 10 assessors are thus precluded given whom at least one item of necessary selection information possesses a value that does not agree with the task information, or a different value precluding an assignment. For example, if the assessor is barred from a specific type of finding, he is precluded just as if he did not possess the necessary qualifications. Assessors are likewise precluded whose time remaining for assessment tasks is not sufficient for the assessment task. It can thereby be provided that a fixed assessment time is associated with specific types of findings; however, it is also conceivable to modify a fixed, predetermined assessment time by a factor dependent on the qualifications or, respectively, experience, for example. It is known that experienced assessors require less time for an assessment task, for example.

The necessary selection information of the "qualification" does not mean possession of an official certification, but rather can indicate a basic competency. This in particular applies for physicians in training or those who are just seeking a specific qualification. Such assessors also qualify in the sense of the necessary selection information; however, additional selection information is then provided that states that the assignment of an additional assessor (in particular with the actual, "official" qualification) is required. This is explained in detail below.

After the number of the assessors was thus limited in Step 10 by the necessary selection information, in Step 11 a numerical value that results from the selection information and weighting factors associated with this is associated by the decision rules with each assessor who is not precluded. The weighting factors ultimately likewise describe decision rules that indicate which properties of the assessor are particularly desirable. For example, if an assessor is only a few findings shy of reaching a qualification, this is strongly weighted, such that his optimally soon achievement of the qualification makes him preferable. However, the equal distribution of assessment tasks to all assessors, or the realization of an optimally inexpensive assessment, can also be correspondingly realized. The focal point of the selection can be shifted accordingly by the weighting factors. The selection information can thereby itself possess a value that can be billed, or a value derived from this can be associated with it, which value then contributes together with the weighting factor to the numerical value. Such scoring systems are known in principle and should not be described in detail here.

In Step 12 the assessment task is now associated with the assessor best suited for the assessment task, thus the assessor who possesses the lowest or the highest numerical value. Naturally, said assessor receives a corresponding message and the data that are required for a finding. These can moreover also be limited. The assessors of all medical facilities 6 are contained in the assessor database 4. For example, if an assessor is selected who does not belong to the medical facility at which the assessment task was created (outsourcing), it can be provided that personal data of the patient (for example the patient's name, address or birth date) are not transmitted to the assessor, for data protection. Other limitations are also conceivable in principle.

After this association in Step 12, in Step 13 it is now checked whether the association of an additional assessor is necessary. For example, this can be the case when the primary assessor is seeking a qualification and his finding must therefore be checked. This can likewise occur in quality assurance, which is explained in detail later with regard to FIG. 4. If such an assignment or association of an additional assessor is necessary (Arrow 14), this assessor is likewise selected and assigned by the method according to the invention (Steps 10-12). However, modified decision rules and/or task information can thereby be used as a basis, as is indicated by Box 15. For example, the additional assessor may already possess a qualification sought by the primary assessor, or even be assigned to the primary assessor for supervision. If two findings should be produced for the purpose of quality assurance, for the most part no modification at all is necessary.

In this context, the method and system 1 according to the invention can directly serve to assist learning and evaluation. The finding of the additional assessor can be brought to the attention of the primary assessor; for example, this can be automatically transmitted via e-mail. The primary assessor then can directly see whether he or she has arrived at the same result, or has selected the correct path, and can learn how the experienced assessor proceeds. It can additionally be provided that the quality of the finding of the primary assessor is registered so that the later evaluation with regard to the attainment of the qualification can be simplified.

Finally, in this exemplary embodiment of the method according to the invention, in Step 16 billing information that is used to account for the assessment task is determined from the selection information and the task information. An invoice is created that is then sent both to the assessor or assessors and to the accounting office of the corresponding medical facility 6. This can also occur in a wholly automatic manner. In a further embodiment of the method according to the invention, a complete accounting component can be inserted into the system 1 according to the invention. A direct connection to an accounting component (provided, for example, to administer the finances of a medical facility) is therefore present, such that the overall accounting can also be set into motion with the assignment.

As was already explained, the additional section information in the assessor database 4 can also include price information, meaning an amount that the respective assessor requests for an assessment task of the specific type; this price information results from the task information. This price information can be modified by the assessor at any time; the user can thus adapt his or her prices to different circumstances. However, this variability of the price information enables the assignment to proceed in the manner of a reverse auction.

Figure 3:
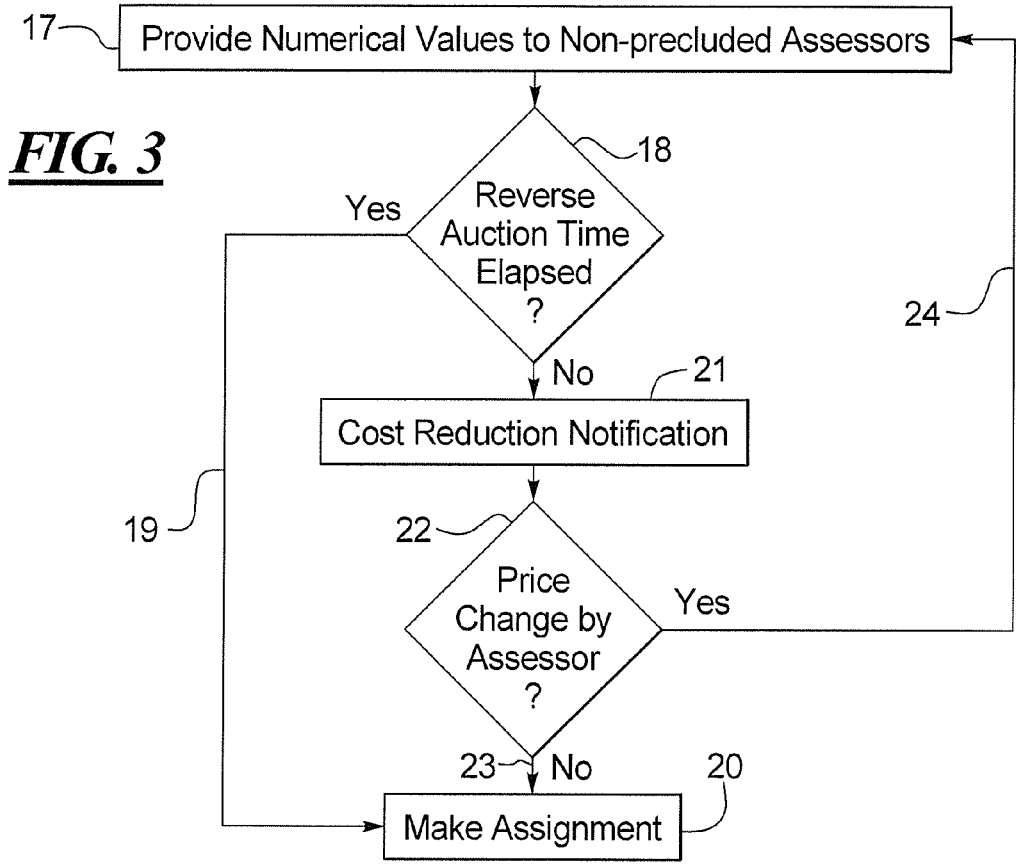
FIG. 3 is a flowchart for a portion of the method according to the invention making use of a reverse auction and FIG. 4 is a flowchart for a portion of the method according to the invention making use of quality assurance measures.

This is represented in detail by the workflow plan in FIG. 3.

The starting point is the list of non-precluded users that are provided with numerical values, which list was determined in Step 11 (represented by the Box 17). In Step 18, it is now initially checked whether a provided running time of the reverse auction has already elapsed. If this is already the case (Arrow 19), the association immediately ensues in Step 20 according to the highest or, respectively, lowest numerical value. However, if the auction has not yet ended, by how much the assessor must lower his costs in order to receive the assignment of the assessment task is determined using the decision rules, the selection information and the task information for each assessor who has not already reached the best numerical value. This occurs in Step 21. Ultimately, given variable price information the numerical values are thereby re-determined until the currently considered user receives the bid. It is accordingly also known what amount this user would have to propose as price information in order to win the reverse auction. In Step 21, every assessor who is not already the lowest bidder receives a message in which this and the necessary amount to win the auction is communicated. This can occur via e-mail, but it is also conceivable to arrange a live auction. Depending on this information, the assessor can now decide whether he or she should change his or her price information, and by what amount. Therefore, in Step 22 it is checked whether an assessor has changed his or her price information. At the same time, it is naturally continuously monitored whether the running time of the reverse auction has already passed. Namely, if the running time has ended (Arrow 23), the assignment ensues in Step 20. However, if price information has changed (Arrow 24), the numerical values (and thus the list) are re-determined and the reverse auction continues in turn.

In such embodiments of the method according to the invention in which price information indicated as part of the selection information is used, it is in principle reasonable to use a maximum price information (in particular as task information) which indicates how much the handling of the assessment task should cost at most. This can also be an exclusion criterion so that an assessor should be excluded if his or her price requirements exceed the maximum costs.

As an alternative to a determination of the price information on the part of the assessor (which is not shown in detail herein), the task information includes price information describing the remuneration to be paid to the assessor. The amount that the assessor is to be compensated is then already established by the medical facility 6 assigning the assessment task. This is particularly advantageous to assure that even difficult assessment tasks for which it is possibly difficult to locate an assessor will be ultimately assigned b the remuneration to be paid being increased with an advancing period of time without the finding taking place.

Of course, an assessor can reject an assessment task assigned to him or her. That assessments task can then be assigned again corresponding to the method according to the invention, wherein the rejecting assessor is excluded.

Furthermore, if information describing a price or cost is used in the method according to the invention, a virtual currency, as is frequently typical in medical facilities, can be used for this purpose. An actual dollar value is associated with the virtual currency only at a point when the budget is clarified.

Figure 4:
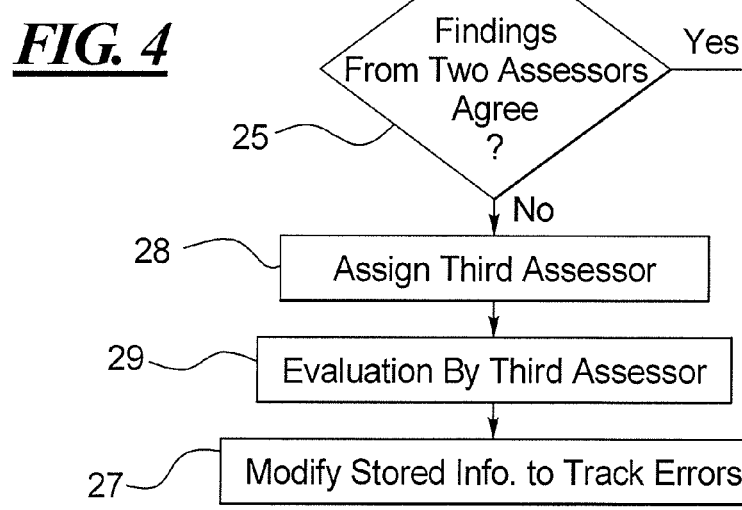

FIG. 4 shows an example of how a quality assurance can be achieved in the method according to the invention. For this purpose, a fixed, specific proportion of assessment tasks is assigned by the system to two assessors. These two assessors (to whom a duplicate assessment is in particular not communicated) now produce a finding independent of one another. The assessor sends these findings (in the simplest case merely indicated in the form of an ICD-10 classification) back to the computer 2, in particular in order to store it together with the patient data in the patient administration system comprising the task database. In Step 25, FIG. 4, in such a case the computer 2 compares the two findings with one another, in particular their ICD-10 classifications. If the findings agree with one another (Arrow 26), the method is ended (Box 27). However, if the findings do not agree, a third assessor to whom the assessment task is assigned is selected by the method in Step 28 (Steps 10-12 in FIG. 2). Modified task information and/or decision rules can thereby be used, for example if a particularly experienced physician should be selected. This assessor then likewise receives the two findings and evaluates these with regard to their correctness. This occurs in Step 29. The number of incorrect findings for the assessor who has produced the incorrect finding (which number is present as selection information in the database) is likewise increased by 1 in Step 30. In this way the proportion of incorrect findings or the number of incorrect findings can continuously be tracked, wherein this selection information in particular also enters into the assignment method.

In the method according to the invention it, if a limit value for incorrect findings (or the proportion of incorrect findings) is exceeded by an assessor, this assessor is barred from the selection procedure. This is noted as selection information in the assessor database 4; it is an item of necessary selection information. At the same time a message is sent to the assessor in which he or she receives a recommendation of measures to increase his or her qualification, for example. In connection with the barring an important motivation tool is thereby provided that, over time, further provides for an overall increase in quality.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for computerized association of an assessor with a medical assessment task, comprising:

in an electronic assessor data base,
storing respective designations of a plurality of medical assessors respectively having expertise in assessing medical information presented in medical images, and selection information respectively associated with each of said assessors, and
storing a plurality of medical assessment tasks, requiring assessment of a medical image, with associated medical task information, and
storing said selection information with a designation as to whether the stored selection information is within a group of items of necessary selection information or within a group of items of additional selection information, and
storing, in said medical task information, a designation as to whether the medical task associated with the medical task information requires said selection information to be in said group of items of necessary selection information; and
entering the respective designation of one of said medical assessment tasks stored in said assessment data base, as an entered medical assessment task designation, into a processor having access to the data base and,
from said processor, accessing, as accessed selection information, the selection information respectively associated with the entered medical assessment task designation and,
in said processor, applying at least one computerized decision rule to said accessed selection information to automatically select a medical assessor, from among the plurality of medical assessors stored in said assessor data base, to perform the current medical assessment task as a selected medical assessor, and configuring said at least one computerized decision rule to, at least initially, preclude medical assessors in said data base lacking an item of necessary selection information from being selected for a medical assessment task in said data base that requires said item of necessary selection information, and emitting a designation in electronic form at an output of the processor that identifies the selected medical assessor.

2. A method as claimed in claim 1 comprising storing, as said item of necessary information, at least one item selected from the group consisting of medical competency qualification of the medical assessor, work hours available to the medical assessor for medical assessment tasks, and at least one bar of the medical assessor from a specific medical assessment task.

3. A method as claimed in claim 1 comprising storing, in said assessor data base, medical assessors associated with respectively different, multiple medical facilities.

4. A method as claimed in claim 1 comprising, in said processor, automatically determining billing information, for charging for implementation of the medical assessment task, from said selection information and said medical task information.

5. A method as claimed in claim 1 comprising storing, as said selection information, information describing medical assessment tasks to be conducted in order to obtain a competency qualification, and a necessary assignment of an additional medical assessor.

6. A method as claimed in claim 5 comprising, when said processor selects a medical assessor from said data base having, in the associated selection information, the necessary assignment of an additional medical assessor, said processor automatically selects and assigns said additional medical assessor.

7. A method as claimed in claim 6 comprising, in said processor, selecting, as said additional medical assessor, a medical assessor in said data base who already possesses a qualification lacked by the selected medical assessor, or an additional medical assessor who is assigned to the selected medical assessor for supervision.

8. A method as claimed in claim 7 comprising automatically informing the selected medical assessor of the selection of the additional medical assessor, or determining and storing a quality of the assessment made by the selected assessor for the medical assessment task.

9. A method as claimed in claim 1 comprising blocking communication of patient data of a patient associated with the medical assessment task to the medical assessor selected for the medical assessment task.

10. A method as claimed in claim 9 comprising using an affiliation of the medical assessor selected for a medical assessment task with a different facility from a facility associated with the patient as a condition for blocking transmittal of said patient data.

11. A method as claimed in claim 1 comprising storing, in said selection information in said data base, at least one item of price information identifying a cost of the assessor for performing the medical assessment task.

12. A method as claimed in claim 11 comprising allowing modification of the price information by the medical assessor.

13. A method as claimed in claim 11 comprising employing a maximum price setting a maximum cost for the medical assessment task as said item of price information in said selection information, and precluding any medical assessor in said assessment data base from being selected for the medical assessment task if that medical assessor has a cost for the medical assessment task that exceeds said maximum cost.

14. A method as claimed in claim 11 comprising employing a virtual currency as said item of price information.

15. A method as claimed in claim 12 comprising automatically informing a medical assessor when a medical assessment task for which that medical assessor is qualified is to be assigned to a different medical assessor.

16. A method as claimed in claim 15 comprising determining, in said processor, an amount by which the notified medical assessor must decrease the medical assessor's cost in order to have the medical assessment task assigned to the notified medical assessor, in said processor using further decision rules, said selection information and said medical task information, and communicating said amount to a user of the processor.

17. A method as claimed in claim 1 comprising storing, in said medical task information in said data base, price information describing remuneration to be paid to the medical assessor selected for the medical assessment.

18. A method as claimed in claim 17 comprising, through said processor, automatically increasing and posting said cost with increasing time without selection of a medical assessor occurring.

19. A method as claimed in claim 1 comprising, in said data base, associating a selected number of the medical assessment tasks stored in the data base with at least two medical assessors stored in the assessor data base and implementing at least one medical assessment task, among said selected number of the medical assessment tasks, with each of said at least two medical assessors.

20. A method as claimed in claim 19 comprising, in said processor, automatically comparing and checking the respective medical assessments made by the at least two medical assessors selected for a medical assessment task and, upon disagreement of said respective medical assessments, automatically assigning through said processor the medical assessment task to a third medical assessor, using further computerized decision rules, and employing a medical assessment made by said third medical assessor to evaluate correctness of the medical assessments respectively made by the at least two medical assessors, and storing a number or proportion of incorrect findings for said at least two medical assessors in said data base in the selection information respectively associated in the data base with said at least two medical assessors.

21. A method as claimed in claim 20 comprising precluding any medical assessor stored in said data base from selection for a medical assessment task if that medical assessor has, in the selection information associated therewith, a designation that the medical assessor has exceeded a limit value for incorrect assessments or a limit value for a proportion of incorrect assessments, and automatically informing that medical assessor of suggested steps to improve said value of incorrect assessments or proportion of incorrect assessments.

22. A method as claimed in claim 1 comprising, in said assessment data base, storing said selection information with weighting factors.

23. A method as claimed in claim 22 comprising, in said assessor data base, associating a numerical value with each medical assessor derived from said weighting factors and, according to said computerized decision rule, selecting a medical assessor from among the medical assessors stored in said assessor data base having a lowest or highest numerical value associated therewith for the medical assessment task.

24. A method as claimed in claim 23 comprising storing, as weighting factors in said data base, factors selected from the group consisting of a time until attainment of competency qualification by the medical assessor, equal distribution of medical assessment tasks to all medical assessors in the data base, and a cost charged by the medical assessor for performing the medical assessment task.

25. A method as claimed in claim 1 comprising including, in said selection information stored in said data base, a necessary time for completion of a medical assessment task.

26. A system for computerized association of an assessor with a medical assessment task, comprising:
   an electronic assessor data base
      in which respective designations of a plurality of medical assessors respectively having expertise in assessing medical information presented in medical images, and
      selection information are stored respectively associated with each of said medical assessors, and
      in which a plurality of medical assessment tasks requiring assessment of a medical image are stored with associated medical task information are stored and in which said selection information is stored with a designation as to whether the stored selection information is within a group of items of necessary selection information or within a group of items of additional selection information, and
      in which, in medical said task information, a designation is stored as to whether the task associated with the medical task information requires said selection information to be in said group of items of necessary selection information;
   a computerized processor having access to said data base;
   an input unit connected to said processor that allows entry of a designation of one of said medical assessment tasks stored in said assessment data base into the processor, as an entered medical assessment task designation; and
   said processor
      being configured to access, as accessed selection information, the selection information respectively associated with the entered medical assessment task designation
      and to apply at least one computerized decision rule to said accessed selection information to automatically select a medical assessor, from among the plurality of medical assessors stored in said assessor data base, to perform the current medical assessment task as a selected medical assessor,
      said at least one computerized decision rule being configured to, at least initially, preclude medical assessors in said data base lacking an item of necessary selection information from being selected for a task in said data base requiring said item of necessary selection information, and
      said processor being configured to emit a designation in electronic form at an output of the processor that identifies the selected medical assessor.

27. A system as claimed in claim 26 wherein said processor is a central server connected with a plurality of workstation computers via a network.

28. A system as claimed in claim 27 wherein said workstation computers are located at respectively different medical facilities.

29. A system as claimed in claim 26 comprising a patient administration system in which said task data base is contained.

* * * * *